US012722026B2

(12) United States Patent
Kim et al.

(10) Patent No.: US 12,722,026 B2
(45) Date of Patent: Sep. 1, 2026

(54) ULTRASONIC MEDICAL DEVICE FOR SKIN TREATMENT AND COOLING CAP THEREFOR

(71) Applicant: WONTECH CO., LTD., Daejeon (KR)

(72) Inventors: Jong Won Kim, Seongnam (KR); Jung Hyun Kim, Seongnam (KR); Young Seok Seo, Sejong (KR); Jang Hyun Mun, Sejong (KR)

(73) Assignee: WONTECH CO., LTD., Daejeon (KR)

( * ) Notice: Subject to any disclaimer, the term of this patent is extended or adjusted under 35 U.S.C. 154(b) by 0 days.

(21) Appl. No.: 19/204,917

(22) Filed: May 12, 2025

(65) Prior Publication Data

US 2026/0224918 A1 Aug. 6, 2026

(30) Foreign Application Priority Data

Feb. 6, 2025 (KR) ........................ 10-2025-0015004

(51) Int. Cl.
*A61B 8/00* (2006.01)
*A61N 7/02* (2006.01)
*A61N 7/00* (2006.01)

(52) U.S. Cl.
CPC ........ *A61N 7/02* (2013.01); *A61N 2007/0034* (2013.01)

(58) Field of Classification Search
CPC .......................... A61N 7/02; A61N 2007/0034
See application file for complete search history.

(56) References Cited

U.S. PATENT DOCUMENTS

2013/0190745 A1* 7/2013 Fourkas ................. A61B 18/02 606/25
2014/0276055 A1* 9/2014 Barthe ................. A61B 8/4466 600/439
2016/0175619 A1 6/2016 Lee
2017/0303888 A1* 10/2017 Jung ........................ A61B 8/42

FOREIGN PATENT DOCUMENTS

KR 10-1671007 B1 10/2016
KR 10-2019-0115586 A 10/2019
KR 10-2021-0044352 A 4/2021
KR 10-2024-0123947 A 8/2024

* cited by examiner

*Primary Examiner* — Joel F Brutus
(74) *Attorney, Agent, or Firm* — Harvest IP Law, LLP

(57) ABSTRACT

Proposed are an ultrasonic medical device for skin treatment and a cooling cap for the ultrasonic medical device. The ultrasonic medical device may include a main body configured to generate electrical energy, and may include a handpiece configured to convert the electrical energy into ultrasonic waves and to emit the ultrasonic waves to the skin. The handpiece may include a wand configured to receive the electrical energy from the main body, and may include an ultrasonic cartridge coupled to the wand and configured to convert the electrical energy into the ultrasonic waves and to emit the ultrasonic waves to the skin through an acoustic permeable window. A cooling cap is coupled to the ultrasonic cartridge. The cooling cap may include a housing having a space therein and having a hollow column shape in which a center portion thereof is penetrated, and may include refrigerant accommodated in the space.

10 Claims, 6 Drawing Sheets

ULTRASONIC MEDICAL DEVICE FOR SKIN TREATMENT AND COOLING CAP THEREFOR

CROSS REFERENCE TO RELATED APPLICATION

The present application claims priority to Korean Patent Application No. 10-2025-0015004, filed Feb. 6, 2025, the entire contents of which are incorporated herein for all purposes by this reference.

BACKGROUND

Technical Field

The present disclosure relates to an ultrasonic medical device for skin treatment and a cooling cap therefor. More particularly, the present disclosure relates to an ultrasonic medical device for skin treatment and a cooling cap therefor, the ultrasonic medical device being configured such that the cooling cap is coupled to a handpiece tip and the ultrasonic medical device is configured to cool a treatment region.

Description of the Related Art

Recently, a medical device for skin treatment and cosmetic treatment utilizing various energy sources has been developed. There are energy sources such as a laser, an RF (high frequency), HIFU (High Intensity Focused Ultrasound), and so on. Among them, a HIFU device is a device applying a non-invasive treatment technology in which a high intensity ultrasonic wave is concentrated on a target tissue by a HIFU technology and heats or ablates the target tissue, and is increasingly used in cosmetic medical treatment for the purpose of skin lifting and so on.

Since a treatment HIFU concentrates high intensity ultrasonic wave energy to a specific region below the skin and causes thermal denaturation only at a focused portion, there is an advantage that thermal damage is applied only to the treatment region where the ultrasonic wave is concentrated, and the skin surface and surrounding tissues are not damaged.

However, in the HIFU treatment, the skin may be heated in the process of causing thermal degeneration in the skin, and considerable pain may be accompanied due to the characteristics of the ultrasonic treatment.

In this situation, such a problem may be mitigated by cooling the treatment region. For example, when the skin is cooled, heat in the treatment region is reduced, and skin sensation is reduced due to cooling, so that pain caused by the treatment is reduced more.

However, in a conventional ultrasonic medical device, since a space inside an ultrasonic cartridge is small, it was difficult to have a structure for cooling the skin. In addition, a flow path supplying a refrigerant is required for cooling, and there is a problem that it is difficult to maintain air tightness at a connection portion between a handpiece and the ultrasonic cartridge when a refrigerant flow path of the handpiece is connected to a refrigerant flow path of the ultrasonic cartridge.

SUMMARY

Accordingly, the present disclosure has been made keeping in mind the above problems occurring in the related art, and an objective of the present disclosure is to provide an ultrasonic medical device for skin treatment and a cooling cap for the ultrasonic medical device capable of cooling a treatment region during ultrasonic treatment.

Another objective of the present disclosure is to provide an ultrasonic medical device for skin treatment and a cooling cap for the ultrasonic medical device capable of cooling a treatment region without having a cooling mechanism and a refrigerant flow path in an ultrasonic cartridge considering a narrow internal space of the ultrasonic cartridge.

The objectives that can be obtained from the present disclosure are not limited to the above-mentioned objectives, and other objectives not mentioned herein will be clearly understood by those skilled in the art from the following description.

In order to achieve the objectives of the present disclosure, according to an aspect of the present disclosure, there is provided an ultrasonic medical d for skin treatment, the ultrasonic medical device including: a main body configured to generate electrical energy; and a handpiece configured to convert the electrical energy into ultrasonic waves and to emit the ultrasonic waves to the skin, wherein the handpiece includes: a wand connected to the main body by a cable and configured to receive the electrical energy from the main body; and an ultrasonic cartridge coupled to the wand, the ultrasonic cartridge being configured to convert the electrical energy into the ultrasonic waves and to emit the ultrasonic waves to the skin through an acoustic permeable window, wherein a cooling cap is coupled to the ultrasonic cartridge, and wherein the cooling cap includes: a housing having a space therein and having a hollow column shape in which a center portion thereof is penetrated; and a refrigerant accommodated in the space.

In order to achieve the objectives of the present disclosure, according to an aspect of the present disclosure, there is provided a cooling cap for a medical device, the cooling cap including: a housing having a space formed therein; and a refrigerant accommodated in the space, wherein the housing has a hollow column shape in which a center portion thereof is penetrated, is configured to be coupled to a handpiece of the medical device emitting energy toward the skin of a human, and is configured to cool the skin through a contact surface of the housing, the contact surface being in contact with the skin.

According to aspects of the present disclosure described above, the ultrasonic medical device for skin treatment and the cooling cap for the ultrasonic medical device that is capable of cooling the treatment region during the ultrasonic treatment are provided.

In addition, since the cooling mechanism in a method in which the cooling mechanism is capable of being attached to and detached from the ultrasonic cartridge is provided, a separate space for cooling is not required to be allocated within the ultrasonic cartridge, and the cooling mechanism is capable of being directly applied to the existing ultrasonic cartridge without any additional design change or modification.

In addition, the cooling cap having a structure in which the cooling cap is capable of being conveniently replaced during the treatment is provided. Therefore, when the temperature of the cooling cap in use increases, the cooling cap may be replaced and a new cooling cap may be used, so that continuous cooling is capable of being provided throughout the treatment time.

In addition, since the operator alone is capable of fixing the cooling cap to the ultrasonic cartridge and using the ultrasonic cartridge, a separate cooling device or an auxiliary operator is not required. This may contribute to lowering the overall treatment cost and the maintenance cost of the ultrasonic medical device.

The effects of the present disclosure are not limited to the above-mentioned effects, and other effects not mentioned herein will be clearly understood by those skilled in the art from the following description.

BRIEF DESCRIPTION OF THE DRAWINGS

The above and other objectives, features, and other advantages of the present disclosure will be more clearly understood from the following detailed description when taken in conjunction with the accompanying drawings, in which.

DETAILED DESCRIPTION

Figure 1:
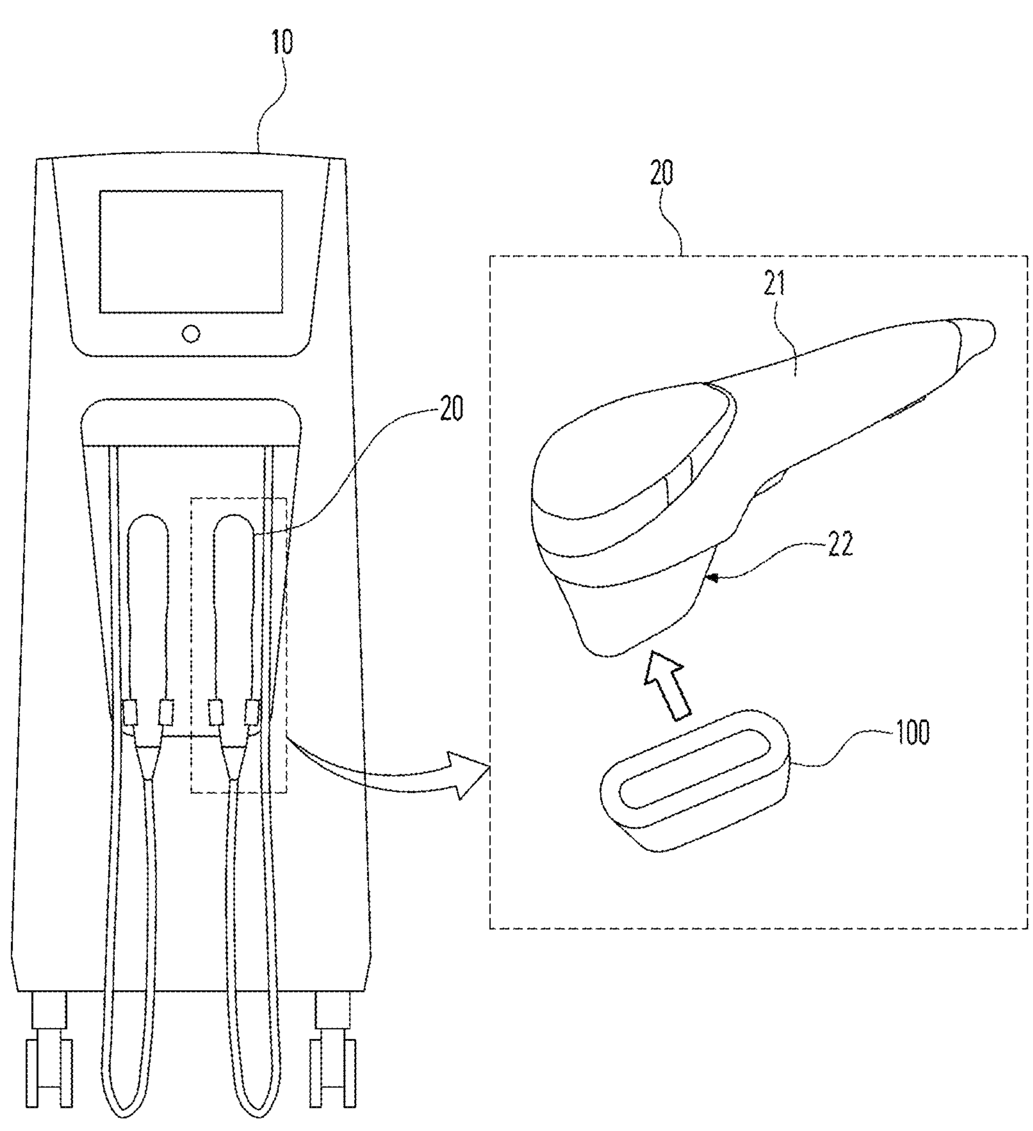
FIG. 1 is a view illustrating an ultrasonic medical device for skin treatment and a cooling cap therefor according to an embodiment of the present disclosure.

Hereinafter, embodiments of the present disclosure will be described below in detail with reference to the accompanying drawings. Advantages and features of the present disclosure, and methods of achieving the same will become apparent with reference to the embodiments described below in detail in conjunction with the accompanying drawings. In adding reference numerals to components throughout the drawings, it is to be noted that like or similar reference numerals designate like or similar components even though the components are illustrated in different drawings. In addition, in describing the present disclosure, when it is determined that a detailed description of a related known configuration or function may obscure the gist of the present disclosure, the detailed description thereof will be omitted.

Unless otherwise defined, all terms (including technical and scientific terms) used herein have the same meaning as commonly understood by those skilled in the technical field to which the present disclosure pertains. It will be further understood that terms, such as those defined in commonly used dictionaries, should not be interpreted in an idealized or overly formal sense unless expressly herein. Terms used in the specification are used to describe embodiments of the present disclosure and are not intended to limit the scope of the present disclosure. In the specification, the terms having a singular form may include plural forms unless otherwise specified.

In addition, in describing the components of the embodiment of the present disclosure, terms such as first, second, A, B, (a), (b), and so on may be used. These terms are only for distinguishing the component from other components, and are not limited to the essence, order, or sequence of the component by the terms. When a component is described as being "connected", "coupled", or "linked" to another component, the component may be directly connected or linked to the other component, or other components may be "connected", "coupled" or "linked" to therebetween.

Hereinafter, embodiments of the present disclosure will be described in detail with reference to the accompanying drawings.

FIG. 1 is a view illustrating an ultrasonic medical device for skin treatment and a cooling cap therefor according to an embodiment of the present disclosure. Referring to FIG. 1, the ultrasonic medical device includes a main body 10 and a handpiece 20. The handpiece 20 may include an ultrasonic cartridge 22, and a removable cooling cap 100 is capable of being coupled to the ultrasonic cartridge 22.

The main body 10 generates electrical energy as an energy source for skin treatment. The generated electrical energy is transferred to the handpiece 20. To this end, a cable for transmitting electrical energy may be connected between the main body 10 and the handpiece 20.

As an embodiment, the main body 10 may be provided with a display, and a user interface for operating the medical device may be displayed on the display.

The handpiece 20 may be configured to convert electrical energy supplied from the main body 10 into ultrasonic waves and to emit the ultrasonic waves to the human skin. Furthermore, the handpiece 20 may include a wand 21 which is connected to the main body 10 by the cable and which is configured to receive electrical energy from the main body 10, and may include the ultrasonic cartridge 22 coupled to the wand 21.

The wand 21 is a portion where an operator holds the handpiece 20 during ultrasonic treatment, and may be provided with a control button for operating the ultrasonic cartridge 22 and so on.

The ultrasonic cartridge 22 includes a transducer (not illustrated) inside the ultrasonic cartridge 22, and converts electrical energy received from the wand 21 into ultrasonic waves through the transducer. The ultrasonic waves converted by the transducer may be emitted to the skin through an acoustic permeable window provided on an output surface of the ultrasonic cartridge 22. That is, the ultrasonic waves converted by the transducer may be emitted to the skin through the acoustic permeable window provided on a surface that is in contact with the skin when the ultrasonic treatment is performed. Here, the acoustic permeable window refers to a component that transmits energy transmitted in the form of sound waves such as ultrasonic waves with zero loss or low loss.

At this time, the cooling cap 100 may be coupled to the ultrasonic cartridge 22.

The cooling cap 100 is a cover-type tip designed to be coupled to the ultrasonic cartridge 22, and the cooling cap 100 may be formed of a metal material having an excellent thermal conductivity.

The cooling cap 100 has a housing having a hollow column shape in which a center portion thereof is penetrated, and the cooling cap 100 is capable of being coupled to the ultrasonic cartridge 22 by a method in which a protrusion portion of the ultrasonic cartridge 22 is inserted into the hollow portion of the housing. For this purpose, a profile of a hollow boundary surface of the housing of the cooling cap 100 may have a shape at least partially corresponding to an outer surface profile of the ultrasonic cartridge 22. When the cooling cap 100 is coupled to the ultrasonic cartridge 22, the acoustic permeable window of the ultrasonic cartridge 22 is positioned in the hollow portion of the cooling cap 100.

Meanwhile, an empty space is formed inside the housing of the cooling cap 100, and a cooled refrigerant may be accommodated in the empty space.

When the ultrasonic treatment is performed while the cooling cap 100 is coupled to the ultrasonic cartridge 22, a bottom surface of the cooling cap 100 is brought into contact with the treatment region. More accurately, the bottom surface of the cooling cap 100 is brought into contact with the skin around the treatment region. At this time, since the cooling cap 100 is cooled by the refrigerant inside the cooling cap 100, the cooling cap 100 cools the treatment region or the skin around the treatment region by a thermal conduction method by being in contact with the skin.

Meanwhile, the ultrasonic cartridge 22 may be provided with various types of ultrasonic cartridges according to a depth of a skin layer to be treated, and the ultrasonic cartridge 22 suitable for a current treatment purpose may be selected and may be coupled to the wand 21 for each treatment. Even in such a situation, the cooling cap 100 may be used universally regardless of the type of ultrasonic cartridge 22 that is replaced.

For example, since the cooling cap 100 is used in a method in which the cooling cap 100 is detached from and attached to an outer surface of the ultrasonic cartridge 22, the cooling cap 100 is not affected by an internal component or a design change of the ultrasonic cartridge 22. Therefore, even when the ultrasonic cartridge 22 is replaced with another type of the ultrasonic cartridge, the existing cooling cap 100 may be used as is if only an outer surface profile of the ultrasonic cartridge 22 is standardized. This increases the usability of the cooling cap 100, and further reduces the introduction cost and the maintenance cost.

Figure 2A:
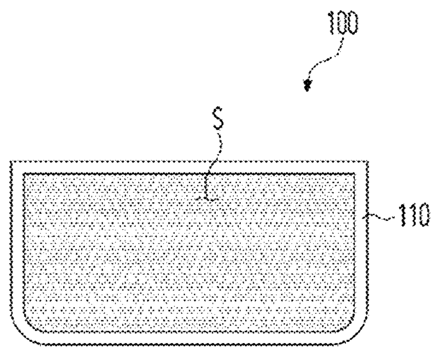
FIG. 2A to FIG. 3B are views illustrating an internal structure of the cooling cap according to various embodiments of the present disclosure.
Figure 2B:
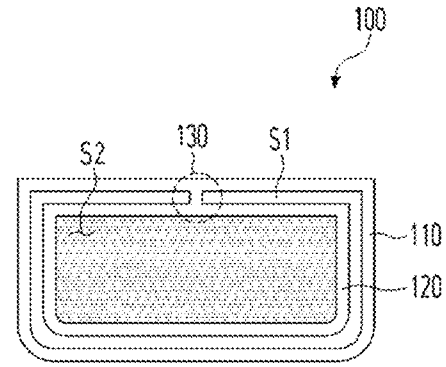

FIG. 2A and FIG. 2B are cross-sectional views illustrating a cooling cap housing according to various embodiments of the present disclosure.

FIG. 2A illustrates an embodiment in which the cooling cap 100 is provided with a housing 110 (a first housing) having a single wall structure, and FIG. 2B illustrates an embodiment in which the cooling cap 100 is provided with housings 110 and 120 (the first housing and a second housing) having a double wall structure.

First, referring to FIG. 2A, the cooling cap 100 is provided with only the first housing 110 on an outer periphery of the cooling cap 100. A space S is formed inside the first housing 110, and the space S is filled with a refrigerant.

As an embodiment, the space S may be a sealed space in which a fluid movement to the outside is blocked by the first housing 110.

The first housing 110 may be formed of a metal material having a high thermal conductivity, and a portion of the space S may remain in a state in which the portion of the space S is not filled with the refrigerant so as to cover a volume change of the refrigerant due to a phase change of the refrigerant accommodated in the space S.

As an embodiment, the first housing 110 may be formed of a material formed of stainless steel, titanium, copper, and/or a combination thereof.

The refrigerant is a material accommodated in the space S in the first housing 110, and acts as a cooling source of the cooling cap 100. Since the refrigerant is required to be accommodated in the sealed space S of the cooling cap 100, it is preferable that the volume change of the refrigerant is required to be as small as possible, and it is preferable that a freezing point of the refrigerant is required to be low so that there is no phase change in a normal storage or a normal use. In addition, in order to maintain a cooling effect of the cooling cap 100 for a long time, it is preferable that a thermal capacity of the refrigerant is large. Meanwhile, since a pressure system is required for thermal circulation in a gaseous refrigerant, the gaseous refrigerant is not suitable as a refrigerant of the cooling cap 100 according to the present disclosure, and a refrigerant that is in a liquid state at the room temperature is suitable as a refrigerant of the cooling cap 100.

As an embodiment, the refrigerant may be a substance that is in a liquid state at the room temperature, does not have a phase change from the room temperature to minus 20 degrees Celsius, and may have a thermal capacity equal to or more than 50 J/K.

As an embodiment, the refrigerant may include tetrafluoroethane, R1234yf, isobutane, and/or chlorodifluoromethane.

Meanwhile, when the cooling cap 100 having the single wall structure as illustrated in FIG. 2A is adopted, the internal structure of the cooling cap 100 is simple, and the manufacturing cost of the cooling cap 100 may be low. However, in this situation, there may be a problem that condensation occurs. That is, due to a large temperature difference between the refrigerant inside the first housing 110 and an external air outside the first housing 110, condensation may occur on the outer surface of the cooling cap 100.

Condensation is a phenomenon in which moisture contained in the air is condensed into water droplets when the air is brought into contact with a cold surface, and may occur more easily when a temperature difference between an inside of the surface and an outside of the surface is large. When condensation occurs on the outer surface of the cooling cap 100, water droplets may fall on a patient's face or skin during the treatment, and may cause discomfort to the patient. In addition, there is a possibility that the ultrasonic cartridge 22 may be damaged due to moisture caused by condensation, and water droplets falling on the skin may permeate into the treatment region, so that the ultrasonic treatment effect may be reduced.

FIG. 2B is a view illustrating the housings 110 and 120 having the double-wall structure for preventing condensation on the cooling cap 100. Referring to FIG. 2B, the cooling cap 100 includes the first housing 110 and the second housing 120.

The first housing 110 is a configuration that is brought into contact with the outer surface of the ultrasonic cartridge 22 when the cooling cap 100 is coupled to the ultrasonic cartridge 22, and defines a first space S1 inside the first housing 110, the first space S1 being separated from the outside of the cooling cap 100. In other words, the first housing 110 may be referred to as an outer wall of the cooling cap 100.

The second housing 120 is a configuration formed in the first space S1, and is completely surrounded by the first housing 110 and is not exposed to the outside of the cooling cap 100 at all. The second housing 120 defines a second space S2 inside the second housing 120, the second space S2 being separated from the first space S1. Furthermore, in the present embodiment, the refrigerant may be accommodated in the second space S2. In other words, the second housing 120 may be referred to as an inner wall of the cooling cap 100.

The first housing 110 and the second housing 120 are spaced apart from each other. Therefore, the first space S1 may also be defined as a space between the first housing 110 and the second housing 120.

As an embodiment, the cooling cap 100 may include a spacer 130 for maintaining a separation between the first housing 110 and the second housing 120.

As illustrated in FIG. 2B, when the cooling cap 100 has the double wall structure formed of the first housing 110 and the second housing 120, condensation due to a temperature difference between the refrigerant and the external air occurs mainly on an outer surface of the second housing 120 (i.e., a portion of the second space S2), and condensation hardly occurs on the outer surface of the first housing 110.

Figure 3A:
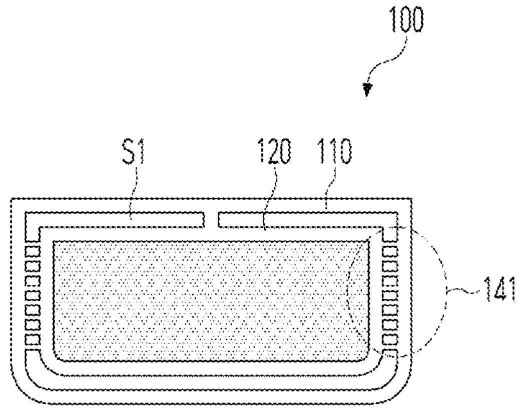
Figure 3B:
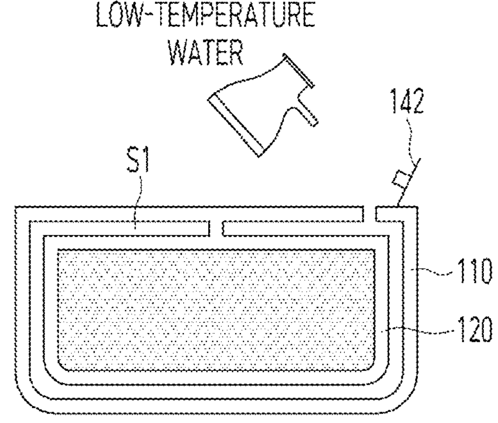

FIG. 3A and FIG. 3B are views illustrating various embodiments for improving thermal conductivity when the cooling cap 100 has the double wall structure.

When the double wall structure is adopted to prevent condensation on the cooling cap 100, condensation on the outside of the cooling cap 100 may be prevented, but the cooling effect may be lowered since a cooling air of the refrigerant is transferred via the first space S1. In order to prevent this situation, following embodiments may be applied.

FIG. 3A is a view illustrating an embodiment of the present disclosure in which a thermal conduction part 141 is provided between the first housing 110 and the second housing 120 of the cooling cap 100 according to an embodiment of the present disclosure.

Referring to FIG. 3A, the thermal conduction part 141 is provided in the first space S1 which is the separation space between the first housing 110 and the second housing 120, and is configured to partially connect the first housing 110 and the second housing 120 to each other. Furthermore, the thermal conduction part 141 may serve to better transfer the cooling air of the refrigerant accommodated in the second housing 120 to the first housing 110 that is in contact with the skin.

As an embodiment, the thermal conduction part 141 may be formed of a metal material having a high thermal conductivity. When a thermal conduction path between the first housing 110 and the second housing 120 is provided by the thermal conduction part 141, the cooling air caused by the refrigerant is better transferred to the first housing 110, and the cooling effect may be increased accordingly.

Meanwhile, when the thermal conduction part 141 having the metal material is provided as illustrated in FIG. 3A, the thermal conductivity between the first housing 110 and the second housing 120 may be effectively increased, but the manufacturing cost may be increased as the processing cost of the cooling cap 100 is increased.

FIG. 3B is a view illustrating an embodiment in which the thermal conductivity between the first housing 110 and the second housing 120 is increased without having the thermal conduction part 141 having the metal material inside the cooling cap 100.

In FIG. 3B, at least one hole is formed in the first housing 110, and an opening and closing part 142 capable of opening and closing the hole is provided on the first housing 110. When the opening and closing part 142 is opened and the hole is opened, the first space S1 may be filled with low-temperature water by injecting the low-temperature water through the hole.

In this situation, since the low-temperature water acts as a thermally conducting material, the thermal conductivity between the first housing 110 and the second housing 120 may be increased.

As an embodiment, the opening and closing part 142 may be formed of a silicone material or a rubber material in order to ensure that one or more holes are sealed well when one or more holes are closed by the opening and closing part 142.

Figure 4A:
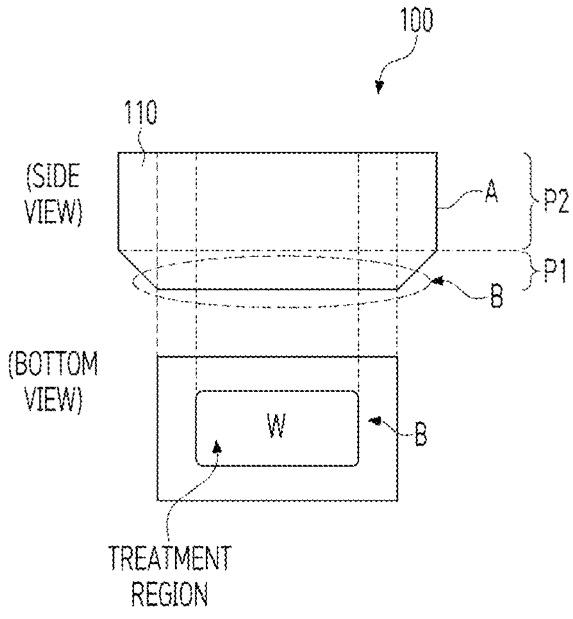
FIG. 4A and FIG. 4B are views illustrating an external structure of the cooling cap according to various embodiments of the present disclosure.
Figure 4B:
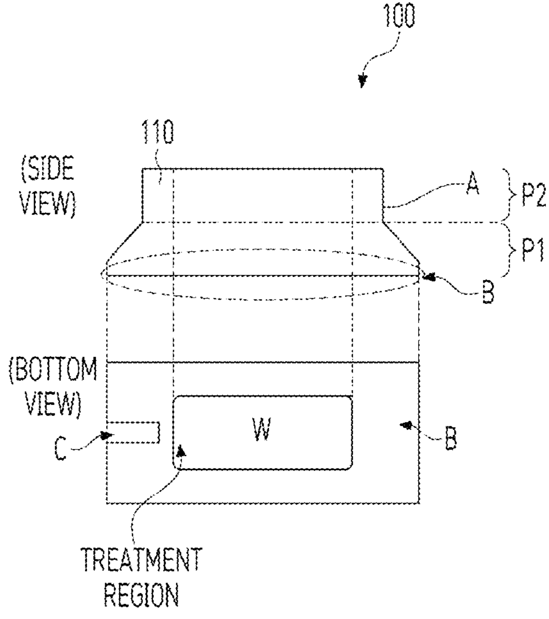

FIG. 4A and FIG. 4B are a side view and a bottom view illustrating the cooling cap according to various embodiments of the present disclosure.

The first housing 110 of the cooling cap 100 may be formed of a metal material. Since the second housing 120 is not mentioned in the present embodiment, the first housing 110 will be briefly referred to as the housing 110.

In a state in which the cooling cap 100 is coupled to the ultrasonic cartridge 22, an acoustic permeable window W of the ultrasonic cartridge 22 is positioned in the hollow portion of the housing 110.

The housing 110 may include a stem part A and a skin contact part B. The stem part A is a portion coupled to the ultrasonic cartridge 22, and a configuration for fixing the cooling cap 100 to the ultrasonic cartridge 22 may be provided in the stem part A. The skin contact part B is a portion which is brought into direct contact with the skin of a subject and which is configured to transfer the cooling air to the skin.

As an embodiment, the housing 110 may include a first part P1 in which an outer diameter thereof increases or decreases toward a first direction (i.e., a skin direction) that is an ultrasonic emission direction. The first part P1 may include the skin contact part B. In addition, the housing 110 may further include a second part P2 in which an outer diameter thereof according to a longitudinal direction thereof is constant. The second part P2 may include the stem part A.

FIG. 4A is a view illustrating an embodiment in which the outer diameter of the first part P1 decreases toward the first direction. FIG. 4A is a view illustrating an embodiment proposed to maximize the field of view for the treatment region.

Since the cooling cap 100 according to the present disclosure is configured such that the cooling cap 100 covers the ultrasonic cartridge 22, a region around the treatment region is blocked by the cooling cap 100 or the housing 110, so that the field of view for the treatment region is limited. This may interfere with the operator in accurately identifying the treatment region.

As illustrated in FIG. 4A, when the housing 110 is manufactured such that the outer diameter of the first part P1 decreases toward the first direction, the field of view for the treatment region and/or for the region around the treatment region may be secured as much as possible. In this situation, the skin contact part B has the outer diameter smaller than the outer diameter of the stem part A.

FIG. 4B is a view illustrating an embodiment in which the outer diameter of the first part P1 increases toward the first direction. FIG. 4B view illustrating an embodiment proposed to maximize the cooling effect on the treatment region.

Since the cooling cap 100 according to the present disclosure has a structure in which the skin contact part B is brought into contact with the skin and transfers the cooling air to the skin, the larger the area of the skin contact part B, the better the cooling effect is realized.

Therefore, as illustrated in FIG. 4B, when the housing 110 is manufactured such that the outer diameter of the first part P1 increases toward the first direction, the housing 110 may have the skin contact part B having a large area, so that the cooling effect may be further increased. In this situation, the skin contact part B has the outer diameter larger than the outer diameter of the stem part A.

Meanwhile, in the present embodiment, an undercut C may be formed on at least a portion of the first part P1 or at least a portion of the skin contact part B.

As illustrated in FIG. 4B, when the area of the skin contact part B is enlarged, the cooling effect may be increased, but the visibility to the treatment region is further limited. Therefore, in order to compensate for this, as illustrated in FIG. 4B, the undercut C for securing visibility may be formed on any position of the first part P1 or the skin contact part B.

According to this, a high cooling effect may be promoted through the skin contact part B having the large area and, at the same time, the visibility to the treatment region may be sufficiently secured through the undercut C.

Figure 5:
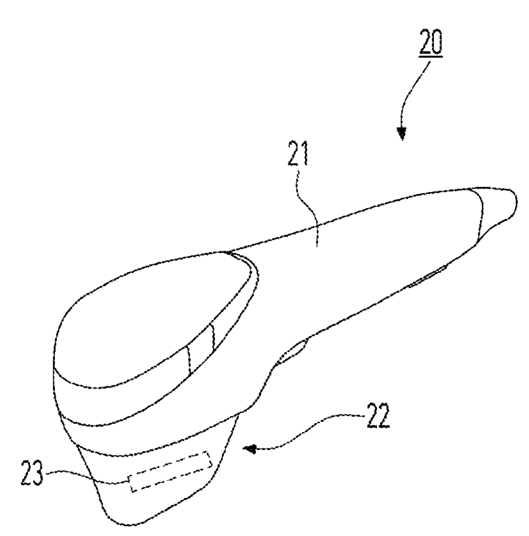
FIG. 5 is a view illustrating a coupling structure between the cooling cap and a handpiece according to an embodiment of the present disclosure.
Figure 5:
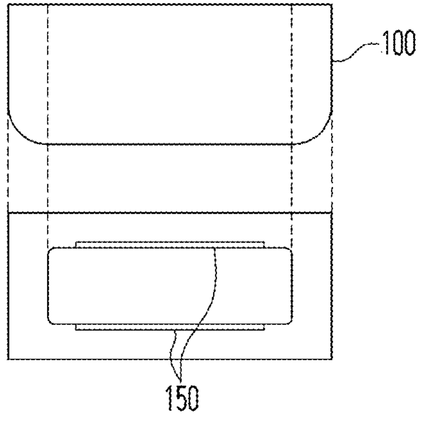

FIG. 5 is a view illustrating a coupling structure between the cooling cap and the handpiece according to an embodiment of the present disclosure. In the present embodiment, an example in which the cooling cap 100 is coupled to the handpiece 20 by using magnetic modules 23 and 150 (a first magnetic module and a second magnetic module) is illustrated.

Referring to FIG. 5, the ultrasonic cartridge 22 of the handpiece 20 may include the first magnetic module 23, and the cooling cap 100 may include the second magnetic module 150. At this time, the first magnetic module 23 and the second magnetic module 150 are magnets, and magnetic attraction may be generated between the first magnetic module 23 and the second magnetic module 150. For example, the first magnetic module 23 and the second magnetic module 150 may be magnets (for example, permanent magnets) of different polarity.

As an embodiment, the first magnetic module 23 may be a strip-type magnet or a block-type magnet provided along the outer surface of the ultrasonic cartridge 22.

As an embodiment, the second magnetic module 150 may be a strip-type magnet or a block-type magnet provided along the hollow boundary surface of the housing 110 of the cooling cap 100.

As an embodiment, the first magnetic module 23 and/or the second magnetic module 150 may include neodymium, ferrite, alnico, samarium cobalt, and so on.

Accordingly, when the cooling cap 100 is coupled to the ultrasonic cartridge 22, the magnetic attraction is generated between the first magnetic module 23 and the second magnetic module 150, so that the cooling cap 100 may be fixed to the ultrasonic cartridge 22.

Meanwhile, when the first magnetic module 23 and the second magnetic module 150 are formed of permanent magnets, there may be difficulties in determining the magnetic force at an appropriate level.

For example, when the first magnetic module 23 and/or the second magnetic module 150 are formed of a magnet having a strong magnetic force, the cooling cap 100 may be stably fixed to the ultrasonic cartridge 22 due to strong mutual attraction, but there may be difficulties when the cooling cap 100 is to be removed after use or for replacement.

Conversely, when the first magnetic module 23 and/or the second magnetic module 150 are formed of a magnet having a weak magnetic force, the cooling cap 100 may be easily removed after use or for replacement. However, since a fixing force of the cooling cap 100 is weak, it may be difficult to stably fix the cooling cap 100 to the ultrasonic cartridge 22.

Alternative embodiments of this will be described in FIG. 6A and FIG. 6B.

Figure 6A:
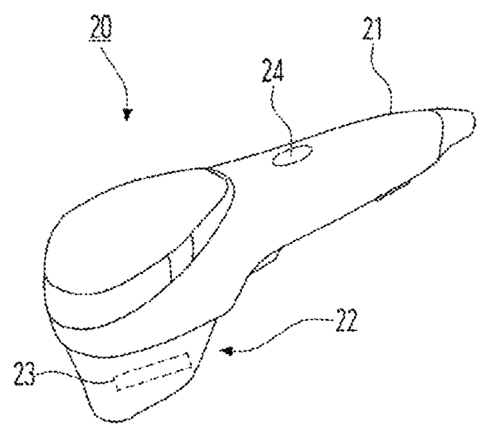
FIG. 6A and FIG. 6B are views illustrating the coupling structure between the cooling cap and the handpiece according to another embodiment of the present disclosure.
Figure 6B:
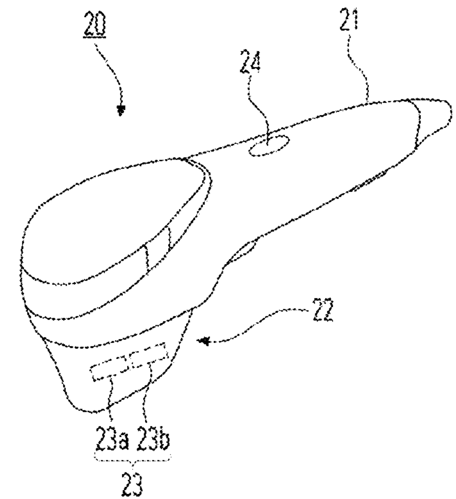

FIG. 6A and FIG. 6B are views illustrating an embodiment in which the first magnetic module 23 is formed of an electromagnet circuit. FIG. 6A illustrates an example in which the first magnetic module 23 is formed of only an electromagnet circuit, and FIG. 6B illustrates an example in which the first magnetic module 23 is formed of an electromagnet circuit 23*a* and a permanent magnet 23*b* having a weak magnetic force.

First, referring to a in FIG. 6A, the handpiece 20 may include the wand 21, the ultrasonic cartridge 22, the first magnetic module 23, and an operation button 24.

The first magnetic module 23 may be controlled by the operation button 24, and may be formed of an electromagnet circuit. An electromagnet is a magnet in which a magnetic field is formed while an electric current flows, and the magnetic field disappears when the electric current does not flow. Since the electromagnet is magnetized only when an electric current flows, it is used in a place where the magnetic property is required to be adjusted. Furthermore, since the intensity of the magnetic property of the electromagnet is capable of being adjusted, an electromagnet having a strong magnetic property is capable of being realized.

The operation button 24 is a button that activates or deactivates the first magnetic module 23 by performing an on-operation or an off-operation, and may be provided on the wand 21. When the operation button 24 is turned-on, the first magnetic module 23 is activated, and a magnetic field is formed around the first magnetic module 23. When the operation button 24 is turned-off, the first magnetic module 23 is deactivated, and the magnetic field surrounding the first magnetic module 23 is deactivated.

When the cooling cap 100 is coupled to the ultrasonic cartridge 22, the operator controls the operation button 24 so that the first magnetic module 23 is activated. At this time, the magnetic field is formed around the first magnetic module 23, and the magnetic attraction is generated between the first magnetic module 23 and the second magnetic module 150, so that the cooling cap 100 is securely fixed to the ultrasonic cartridge 22.

When the cooling cap 100 is removed from the ultrasonic cartridge 22, the operator controls the operation button 24 so that the first magnetic module 23 is deactivated. At this time, the magnetic field around the first magnetic module 23 is deactivated, so that the magnetic attraction no longer acts between the first magnetic module 23 and the second magnetic module 150. Accordingly, the cooling cap 100 is capable of being easily separated from the ultrasonic cartridge 22.

Meanwhile, in the embodiment illustrated in FIG. 6A, when the first magnetic module 23 is deactivated by the operator unintentionally pressing the operation button 24 during the treatment, there is a possibility that the cooling cap 100 is immediately removed, and the cooling cap 100 falls on the face of the subject and causes an injury.

As a complementary embodiment of this situation, an embodiment further including the permanent magnet 23*b* having the weak magnetic force in the first magnetic module 23 will be described with reference to FIG. 6B.

Referring to FIG. 6B, the first magnetic module 23 includes the permanent magnet 23*b* having the weak magnetic force along with the electromagnet circuit 23*a*.

Here, the permanent magnet 23*b* having the weak magnetic force means a permanent magnet having a magnetic force equal to or less than a predetermined strength, and the permanent magnet having a level of magnetic force capable of fixing the cooling cap 100 when the cooling cap 100 is coupled to the ultrasonic cartridge 22, but the fixing force of the permanent magnet is weak so that the cooling cap 100 is capable of being separated even when a small external force is applied. A magnetic force value of the permanent magnet 23*b* having the weak magnetic force may be determined differently according to the weight of the cooling cap 100 and the intensity of the magnetic force of the second magnetic module 150. Accordingly, the magnetic force value of the permanent magnet 23*b* having the weak magnetic force may be determined to a specific value when a detailed design specification of the cooling cap 100 is determined.

The operation of the operation button 24 and the operation of the electromagnet circuit 23*a* are the same as described in FIG. 6A.

That is, the electromagnet circuit 23*a* of the first magnetic module 23 is activated or deactivated by the on-operation or the off-operation of the operation button 24. Therefore, when the cooling cap 100 is coupled to the ultrasonic cartridge 22, the operator controls the operation button 24 so that the electromagnet circuit 23*a* is activated. When the cooling cap 100 is removed from the ultrasonic cartridge 22, the operator controls the operation button 24 so that the electromagnet circuit 23*a* is deactivated.

However, in the present embodiment, since the permanent magnet 23*b* having the weak magnetic force is additionally provided, the operation of the operation button 24 and the coupling and/or the separation of the cooling cap 100 may be more stably performed.

For example, when the cooling cap 100 is coupled to the ultrasonic cartridge 22, the cooling cap 100 is capable of being attached to the ultrasonic cartridge 22 before the operation button 24 is turned-on and the electromagnet circuit 23*a* is activated. At this time, although the operation button 24 has not yet been operated, the cooling cap 100 is fixed to the ultrasonic cartridge 22 force by the permanent magnet 23*b* having the weak magnetic force. Then, when the electromagnet circuit 23*a* is activated by turning on the operation button 24, the strong magnetic field is formed by the electromagnet circuit 23*a*, and the cooling cap 100 is securely fixed to the ultrasonic cartridge 22.

As another example, when the cooling cap 100 is separated from the ultrasonic cartridge 22, the cooling cap 100 is weakly fixed to the ultrasonic cartridge 22 by the permanent magnet 23*b* having the weak magnetic force even when the operation button 24 is turned-off. Therefore, even when the operation button 24 is accidentally pressed during the treatment, the cooling cap 100 is not immediately removed, that an unexpected accident caused by an operation error of the operation button 24 is prevented.

Meanwhile, when the operation button 24 is turned-off and the cooling cap 100 is separated from the ultrasonic cartridge 22 by applying a slight amount of external force, the cooling cap 100 is capable of being removed without difficulty since the fixing force by the permanent magnet 23*b* having the weak magnetic force is not large.

According to the embodiments of the present disclosure described above, the ultrasonic medical device for skin treatment that is capable of cooling the treatment region during the ultrasonic treatment and the cooling cap for the ultrasonic medical device may be provided. Particularly, since the cooling mechanism in a method in which the cooling mechanism is capable of being attached to and detached from the ultrasonic cartridge is provided, a separate space for cooling is not required to be allocated within the ultrasonic cartridge, and the cooling mechanism is capable of being directly applied to the existing ultrasonic cartridge without any additional design change or modification.

In addition, the cooling cap having a structure in which the cooling cap is capable of being conveniently replaced during the treatment is provided. Therefore, when the temperature of the cooling cap in use increases, the cooling cap may be replaced and a new cooling cap may be used, so that continuous cooling is capable of being provided throughout the treatment time. In addition, since the operator alone is capable of fixing the cooling cap to the ultrasonic cartridge and using the ultrasonic cartridge, a separate cooling device or an auxiliary operator is not required, which may contribute to lowering the overall treatment cost and the maintenance cost of the ultrasonic medical device.

The embodiments of the present disclosure are described above with reference to the accompanying drawings. It should be apparent to a person of ordinary skill in the art to which the present disclosure pertains that the present disclosure can be implemented into other embodiments without modification to the technical idea and essential features thereof. Therefore, it should be understood that the embodiments described above are illustrative in all respects and not restrictive. The scope of the present disclosure should be construed as being covered by the scope of the appended claims, and all technical ideas falling within the scope of the claims should be construed as being included in the scope of the present disclosure.

What is claimed is:

1. An ultrasonic medical device for skin treatment, the ultrasonic medical device comprising:

a main body configured to generate electrical energy; and a handpiece configured to convert the electrical energy into ultrasonic waves and to emit the ultrasonic waves to skin, wherein the handpiece comprises:

a wand connected to the main body by a cable and configured to receive the electrical energy from the main body; and an ultrasonic cartridge coupled to the wand, the ultrasonic cartridge being configured to convert the electrical energy into the ultrasonic waves and to emit the ultrasonic waves to the skin through an acoustic permeable window, wherein a cooling cap is coupled to the ultrasonic cartridge, and wherein the cooling cap comprises:

a housing having a space therein and having a hollow column shape in which a center portion thereof is penetrated; and a refrigerant accommodated in the space-, wherein the cooling cap further comprises:

a first housing configured to be brought into contact with an outer surface of the ultrasonic cartridge when the cooling cap is coupled to the ultrasonic cartridge, the first housing defining a first space therein, in which the first space is separated from an outside of the cooling cap; and a second housing formed in the first space, the second housing defining a second space therein, in which the second space is separated from the first space, wherein the first housing and the second housing are at least partially spaced apart from each other, and wherein the refrigerant is accommodated in the second space.

2. The ultrasonic medical device of claim 1, wherein the cooling cap has a shape in which a profile of a hollow boundary surface of the housing is at least partially corresponding to an outer surface profile of the ultrasonic cartridge.

3. The ultrasonic medical device of claim 1, wherein the cooling cap further comprises a thermal conduction part which partially connects the first housing and the second housing to each other and which provides a thermal conduction path between the first housing and the second housing.

4. The ultrasonic medical device of claim 1, wherein the refrigerant is a substance that is in a liquid state at the room temperature, does not have a phase change from the room temperature to minus 20 degrees Celsius, and has a thermal capacity equal to or more than 50 J/K.

5. The ultrasonic medical device of claim 1, wherein the housing comprises a first part in which an outer diameter thereof increases toward a first direction that is an emission direction of the ultrasonic waves.

6. The ultrasonic medical device of claim 5, wherein an undercut is formed on at least a portion of the first part.

7. An ultrasonic medical device for skin treatment, the ultrasonic medical device comprising:

a main body configured to generate electrical energy; and a handpiece configured to convert the electrical energy into ultrasonic waves and to emit the ultrasonic waves to skin, wherein the handpiece comprises:

a wand connected to the main body by a cable and configured to receive the electrical energy from the main body; and an ultrasonic cartridge coupled to the wand, the ultrasonic cartridge being configured to convert the electrical energy into the ultrasonic waves and to emit the ultrasonic waves to the skin through an acoustic permeable window, wherein a cooling cap is coupled to the ultrasonic cartridge, wherein the cooling cap comprises:

a housing having a space therein and having a hollow column shape in which a center portion thereof is penetrated; and a refrigerant accommodated in the space, and wherein the ultrasonic cartridge comprises a first magnetic module, wherein the cooling cap further comprises a second magnetic module, and wherein the cooling cap is configured to be fixed to the ultrasound cartridge by a magnetic attraction between the first magnetic module and the second magnetic module.

8. The ultrasonic medical device of claim 7, wherein the second magnetic module comprises a strip-type magnet or a block-type magnet provided along a hollow boundary surface of the housing.

9. The ultrasonic medical device of claim 8, wherein the first magnetic module comprises an electromagnet circuit in which an operation thereof is controlled by an operation of an operation button.

10. The ultrasonic medical device of claim 8, wherein the first magnetic module comprises a strip-type magnet or a block-type magnet provided along an outer surface of the ultrasonic cartridge.

* * * * *